(12) United States Patent
Urion

(10) Patent No.: US 11,452,636 B2
(45) Date of Patent: Sep. 27, 2022

(54) CANNULA

(71) Applicant: FRANCE CHIRURGIE INSTRUMENTATION SAS (FCI), Paris (FR)

(72) Inventor: Stéphane Urion, Cromary (FR)

(73) Assignee: FRANCE CHIRURGIE INSTRUMENTATION SAS (FCI), Paris (FR)

(*) Notice: Subject to any disclaimer, the term of this patent is extended or adjusted under 35 U.S.C. 154(b) by 327 days.

(21) Appl. No.: 16/880,233

(22) Filed: May 21, 2020

(65) Prior Publication Data
US 2020/0276049 A1 Sep. 3, 2020

Related U.S. Application Data

(63) Continuation of application No. 13/935,632, filed on Jul. 5, 2013, now abandoned.

(30) Foreign Application Priority Data

Jul. 6, 2012 (FR) ..................................... 12 01919

(51) Int. Cl.
*A61F 9/00* (2006.01)
*A61F 9/007* (2006.01)

(52) U.S. Cl.
CPC ................. *A61F 9/00772* (2013.01)

(58) Field of Classification Search
CPC .............. A61F 9/00772; A61F 9/00781; A61F 9/0017; A61F 9/007
See application file for complete search history.

(56) References Cited

U.S. PATENT DOCUMENTS

| | | | |
|---|---|---|---|
| 5,501,232 A | 3/1996 | Ritleng | 128/898 |
| 5,863,366 A | 1/1999 | Snow | 156/143 |
| 6,042,581 A | 3/2000 | Ryan et al. | 606/45 |
| 6,117,116 A | 9/2000 | Walsh | 604/264 |
| 8,864,746 B2 * | 10/2014 | Becker | A61M 5/007 604/8 |
| 2002/0151903 A1 | 10/2002 | Takei et al. | 606/99 |
| 2004/0064128 A1 | 4/2004 | Raijman et al. | 604/523 |
| 2004/0204704 A1 | 10/2004 | Tamplenizza et al. | 606/16 |

OTHER PUBLICATIONS

French Search Report dated Nov. 16, 2012 in related application FR1201919.

* cited by examiner

*Primary Examiner* — Camtu T Nguyen
(74) *Attorney, Agent, or Firm* — Renner, Kenner, Greive, Bobak, Taylor & Weber

(57) ABSTRACT

A cannula includes a hollow cylindrical body which is open at one end and closed at the other end. A slot extends from the open end toward the closed end, terminating with an opening that is larger in width than the slot, the width being measured in a direction perpendicular to the longitudinal direction in which the slot extends. The opening allows the passage of a guide wire for relative sliding. The configuration of the cannula is such that the end of the wire coming out of the cannula through the opening cannot, once inserted into the openings, penetrate into the part of the cannula beyond the opening between the latter and the closed end of the cannula. Related methods for inserting a tube shaped probe into a tear duct are disclosed.

12 Claims, 2 Drawing Sheets

CANNULA

CROSS-REFERENCE TO RELATED APPLICATION

This application is a continuation application of U.S. patent application Ser. No. 13/935,632, filed on Jul. 5, 2013, and which is incorporated herein by reference.

TECHNICAL FIELD

The present invention relates to an intubation cannula for an intubation system, in particular a monocanalicular or bicanalicular system, known as a Ritleng system, which comprises an intubation cannula, a guide wire and a probe, in particular in the form of a tube, in particular made of silicone, the latter being designed to be inserted into the tear duct. The present invention also relates to an intubation system of this kind.

BACKGROUND ART

The objective is to introduce the probe in the form of a silicone tube into the tear ducts. To achieve this, first of all the tear ducts of the patient are catheterised by means of the cannula, which is open at one end and closed at the opposite end and comprises a slot extending along a generator from the open end towards the closed end, up to an opening formed in the lateral wall of the cannula, said opening having a greater width dimension (measured perpendicular to the longitudinal axis of the cannula) than the slot. Then the wire connected to the silicone tube is inserted inside the cannula and is pushed out of the latter through said opening into the nasal cavity. The wire, usually made of prolene, is then retrieved from the nasal cavity and the cannula is removed from the tear ducts by sliding it over the wire and disconnecting it at a narrowed section of the latter by removing said narrowed section through the slot formed over the length of the cannula. Once the cannula has been removed, the wire made of prolene is pulled from the side of the nasal cavity to insert the tube probe, which is made of silicone and is joined to the other end of the wire, into the tear ducts. A Ritleng system of this kind is described in European patent EP 0623329. The end of the wire, with a diameter of 0.4 mm is easily inserted into the cannula, with a diameter of 0.5 mm and is easily pushed so as to come into contact with the base of the cannula, opposite the opening through which the wire is inserted, beyond the opening.

Although this Ritleng system represented a clear advancement for the introduction of the silicone tube probe into the tear duct, it is desirable to make the latter less traumatic for patient.

DISCLOSURE OF THE INVENTION

The present invention aims to overcome the disadvantages of the prior art by proposing methods of inserting a tube shaped probe into a tear duct.

Thus when a surgeon slides the guide wire into the cannula for it to come out at the free end on the side of the nasal cavity through the opening, he will not find it difficult to access the free end, which contrary to the case of cannulas from the prior art (see in particular EP 062329), cannot get trapped in the inner cavity of the cannula beyond the opening at the opposite side of the introduction opening of the wire between the opening and the base of the cannula, the inner base of the cannula being at the end of the opening and forming a guide ramp for the wire towards the outside. The retrieval operation by the practitioner of the end of the wire is thus less traumatic for the patient and the surgeon does not need to fumble around in the nasal cavity to look for the wire caught in the cannula. The operation is therefore also simpler for the surgeon.

According to an advantageous embodiment the space between the end of the opening in longitudinal direction towards the closed outer end and the closed outer end is solid such that the inner wall of the base of the cannula is located substantially at the end of the opening.

According to a preferred embodiment, the cannula comprises an inner wall forming the base of the cannula which closes the space between the end of the opening in the direction of the closed outer end and said closed outer end.

Preferably, the inner wall of the base of the cannula, which is located substantially at the end of the opening in longitudinal direction towards the closed outer end, forms an angle of less than 90°, in particular between 15 and 30°, with the longitudinal axis, so as to thus form a guide ramp towards the top, that is towards the opening, for the end of the wire that is slid into the cannula by pushing it through the opening of the cannula.

The present invention also relates to a system, known as a Ritleng system, comprising a cannula according to the invention and an intubation probe comprising at least one part in the form of a tube made of a flexible, biocompatible material, in particular silicone, joined to a guide wire, made in particular of prolene, one end of which for the mutual connection of the probe and the wire, is introduced into the tube through an opening of the latter.

Preferably, the tube of the probe comprises a section, from the side of the opening of the tube through which the end of the wire is introduced into the tube, having a bevelled shape, the exterior diameter of the tube, along the section, increasing from the opening.

Preferably, the thickness of the tube increases from the opening along the bevelled section then is constant thereafter.

By bevelling the part in the form of a tube of the probe which follows the wire joined to the probe, it is ensured that in the passage between the wire and the silicone tube the transition is more flexible, and consequently when the probe is pulled by the wire to pass into the tear ducts the tube, because of this bevelled form, penetrates more easily and follows the wire more easily, in particular without the edge of the tube turning in on itself, which is less traumatic for the walls of the tear duct.

BRIEF DESCRIPTION OF THE DRAWINGS

By way of example, an embodiment of the invention will now be described with reference to the drawings in which.

PREFERRED EMBODIMENT FOR CARRYING OUT THE INVENTION

Figure 1:
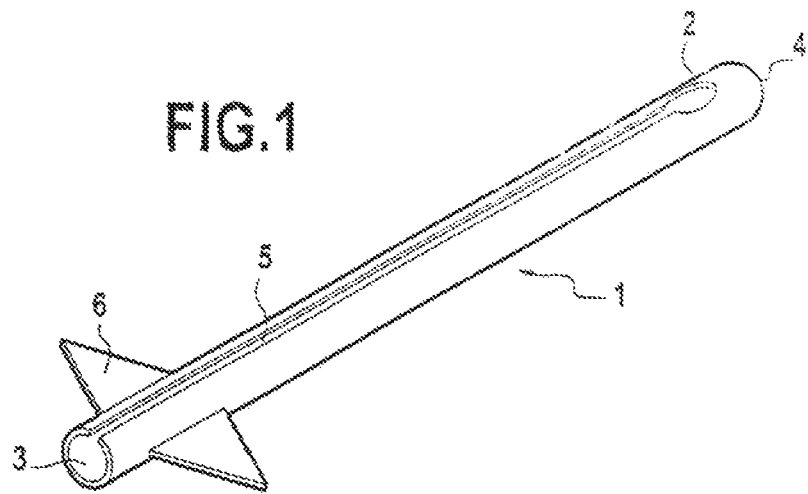
FIG. 1 is a view from above of a cannula of an intubation system according to the invention.

FIG. 1 shows a cannula of a system according to the invention. Said cannula 1 is formed by a hollow circular cylindrical body made from a semi-rigid material, for example stainless steel or a thermoplastic material, in particular PEEK or polyarylamide, open at a proximal end 3 and closed at the opposite distal end 4.

The cannula 1 comprises a longitudinal slot 5 which extends along a generator of the cylinder, from the open proximal opening 3 in the direction of the closed end 4 up to an opening 2 with a larger width (measured perpendicular to the longitudinal axis of the cylinder, which is parallel to the longitudinal slot) than that of slot 5.

The opening 2, viewed from above as in FIG. 1, has an elliptical form, the small diameter of which is perpendicular to the longitudinal axis and the large diameter of which is parallel to the axis of the slot. The small diameter is greater than the thickness of the gap of the slot.

Gripping fins 6 project laterally from the cannula, adjacent to the proximal opening 3.

Figure 2:
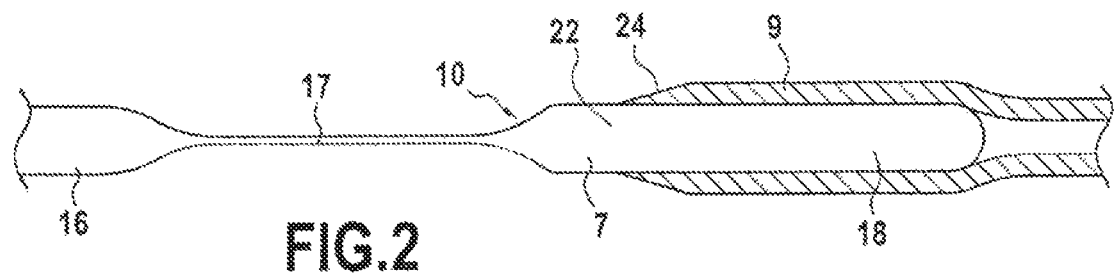
FIG. 2 shows an intubation assembly forming a Ritleng probe according to the invention, which shows the connection between the silicone tube and the guide wire.
Figure 3:
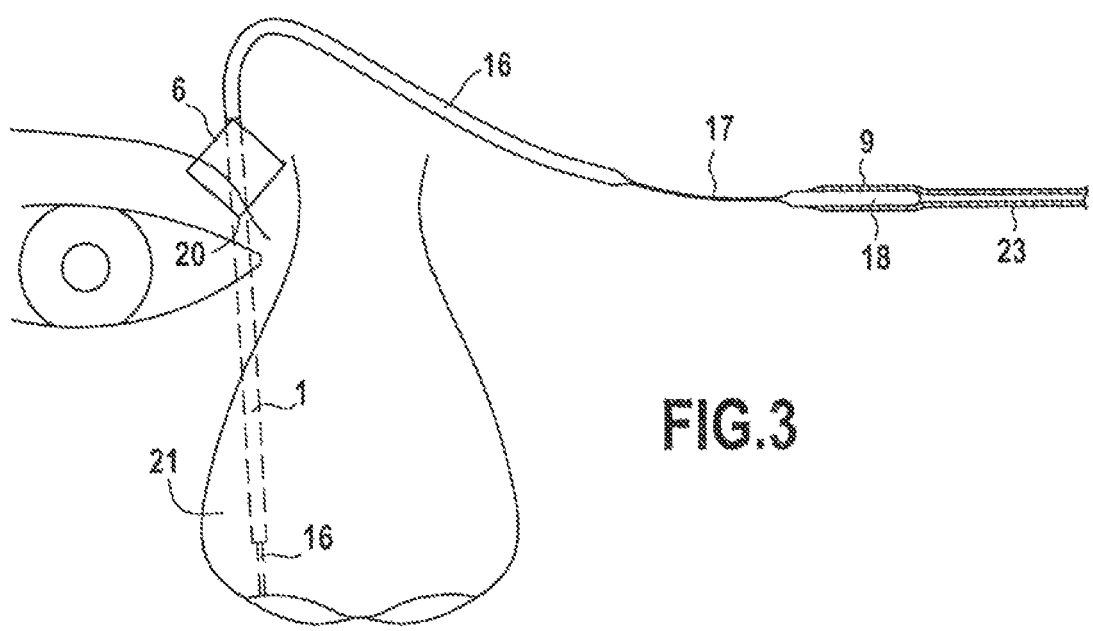
FIG. 3 is a schematic view describing the method of inserting the silicone tube into the tear duct.

FIG. 2 shows in part an intubation assembly 10 known as a Ritleng system. This Ritleng type intubation assembly 10 is formed by a wire 7, in particular made of prolene or another biocompatible and similarly resilient material, and a tube probe 9 made of silicone.

The wire has three sections, namely an end section 16 with a large diameter followed by an intermediate section 17 with a smaller diameter, the latter followed by an opposite end section 18 with a large diameter. The diameter of the section 16 with a large diameter is such that it can pass into the tube and into the opening 2 but not into the slot 5. The diameter of the intermediate section 17 with a smaller diameter is such that it can pass into the slot 5.

The probe 9 is formed by a hollow circular cylinder with a wall width of preferably between 0.15 mm and 0.5 mm. It is made in particular of silicone or another similar material.

The opposite end section 18 with a large diameter is inserted into the silicone tube 9 for their mutual connection. Said connection can be performed by inserting with force or by means of a tight fit. It is also possible to connect them by adhesion or any other similar method, for example ultrasonic welding.

The insertion of the tube probe 9 into the tear duct is performed in the following manner:

First of all the cannula 1 is inserted into the tear duct by penetrating through the exterior entry point 20 from the side of the eye up to the exit 21 opening into the nasal cavity.

Once the cannula has been inserted section 16 is slid along until the end of the section comes out of the cannula through the opening 2. The surgeon then takes hold of the end coming out of section 16 and by taking hold of it, for example with a suitable pair of tweezers (not shown), he pulls the cannula 1 by the fins out of the tear duct. To insert the tube probe 9 into the tear duct, the opposite end section 18 with a large diameter is inserted into the cannula and by taking hold of the latter by the fins 6, the assembly (cannula and wire) is inserted into the tear duct from the exterior from the side of the eye until one end of the wire passing through the opening 2 of the cannula comes out through the inside of the nostrils. Then the cannula 1 is removed by pulling on the fins 6. The cannula slides along the wire until it reaches the intermediate section 17 which can then be passed through the slot 5 of the cannula to release the latter from its cooperation with the wire.

Once the cannula 1 has been removed, the wire is pulled by its end coming from the tear duct from the side of the nostril until the silicone tube 9, joined to section 18 of the wire, is inserted into the tear duct. Once the silicone tube 9 has been inserted into the tear duct, the guide wire which hangs from the exterior of the nostrils is cut.

The probe 9 is formed here by a tube open on both sides. From the side of the opening 22 through which section 16 is introduced into the tube 9 for the mutual connection thereof, the lateral wall 23 defining the tube has a thickness which varies such that a section (24) of the edge of the tube 9 has a bevelled form.

During the installation of the silicone tube 9 by pulling the guide wire, the fact that the leading edge of the guiding tube 9 has a bevelled form makes it possible to assist with the installation of the silicone tube 9 such that, unlike the prior art, there is no leading edge with a sharp edge which knocks against the wall of the tear duct, thus avoiding damage to this wall of the tear duct and/or the edge of the tube 9 does not turn over which may cause the disconnection of section 16 and the tube 9 before reaching the final desired position of the latter in the tear duct and therefore there is no poor positioning of the silicone tube 9 making it necessary to locate it, then restart the whole operation with a new silicone tube. Thus, according to the invention, by means of the bevelling or chamfering the insertion is less traumatic for the wall of the tear duct and has a greater rate of success.

Figure 4:
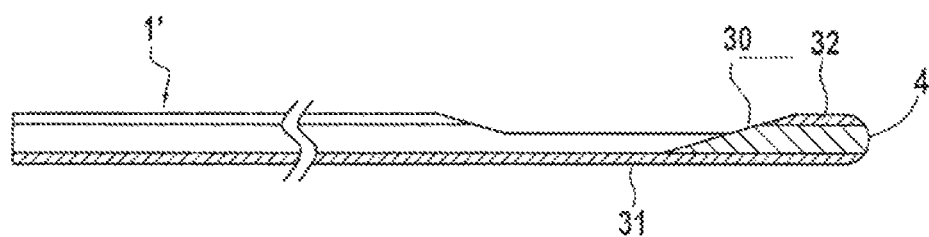
FIG. 4 shows another embodiment of a cannula of an intubation system according to the invention, shown in longitudinal cross section.
Figure 5:
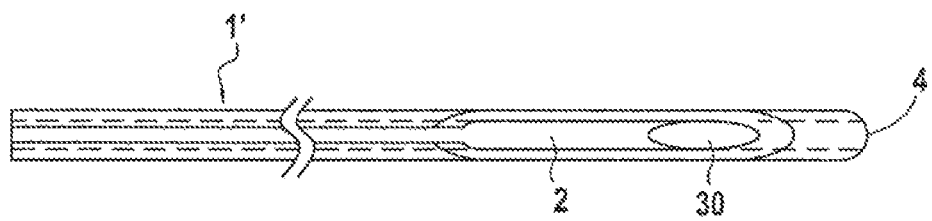
FIG. 5 is view from above of the cannula of FIG. 4.

FIGS. 4 and 5 show a cannula 1' according to another embodiment which can also be used in the intubation system described above in place of the cannula 1. Identical parts of the two cannulas 1 and 1' are represented by the same reference numbers.

Beyond the opening 2 and up to the opposite distal end 4, the cannula is solid such that the guide wire, during its insertion into the cannula, cannot penetrate into the cannula beyond the opening 2, abutting against the inner surface 30 of the base of the cannula. Said inner surface 30 is bevelled, being inclined by about 18° relative to the longitudinal axis of the cannula.

The inner surface 30 forming the base of the cannula is planar. In longitudinal cross section, as shown in FIG. 4, it has the form of a straight line which extends from a lower point 31 of the inner side wall of the cannula from the side opposite the slot up to an upper point 32 of the side wall of the cannula from the side of the slot, the upper point 32 being closer to the distal end 4 of the cannula than point 31. In place of a planar form it is also possible however to have a slightly curved, concave or convex form. The function of this surface 30 forming the inner base of the cannula is to guide the end of the guide wire to make it exit through the opening 2 during the insertion stage of the wire into the cannula, and thus prevent it from penetrating into an area of the cannula beyond the opening 2, between the latter and the distal end, to prevent, as in the prior art, the wire from getting stuck and requiring the surgeon to retrieve the stuck wire from the space beyond the opening.

According to another embodiment, which is not shown, it is possible not to fill the space beyond the opening 2 but to close it with a wall which then forms an abutting and guiding surface for the guide wire with the same function as the surface 30.

What is claimed is:

1. A method for inserting a tube-shaped probe into a tear duct, comprising the steps of:
    providing the tube-shaped probe being formed by a tube having a lateral wall defining the tube, wherein a terminating end of the tube has a thickness that varies to create a beveled form;
    providing a wire, said wire having a distal end section, an intermediate narrowed section and a proximal end section;
    connecting said wire distal end to said tube-shaped probe by inserting said wire distal end into said tube-shaped probe and connecting said wire distal end to said tube-shaped probe by a tight fit, adhesion, or ultrasonic welding;

providing a cannula, said cannula comprising an elongated hollow cylindrical body and extending along a longitudinal axis between a front end and a rear end, said elongated hollow cylindrical body having a front end opening at said front end, said front end opening having a dimension allowing passage therethrough of said wire, a slot extending from said front end towards said rear end, said slot having a slot width, as measured perpendicularly to said longitudinal axis, and being terminated by a lateral opening having a lateral width larger than said slot width, so that said proximal end section can pass through said lateral opening but not through said slot, said lateral opening being distant from said rear end, wherein said cannula comprises an inner wall defining a space inside the cannula between said lateral opening and said rear end, wherein said inner wall forms at said lateral opening an angle of less than 90° with said longitudinal axis, wherein said method comprises the further following steps of:

inserting said cannula into the tear duct by penetrating through an exterior entry point from the side of the eye up to an exit opening into the nasal cavity;

sliding said wire proximal end section inside said cannula from said front end opening towards said lateral opening until having said wire proximal end section coming out of said cannula through said lateral opening;

pulling from the eye side said cannula out of the tear duct while taking hold of said wire proximal end section which came out of said lateral opening;

inserting said wire distal end into said cannula, while taking hold of the cannula;

inserting said cannula and said wire distal end section into the tear duct from the exterior from the side of the eye until the wire proximal end section passing through the lateral opening comes out through the inside of the nostrils;

pulling said wire proximal end section out from said nostril, thereby advancing the said wire distal end and said tube-shaped probe connected thereto, until said tube-shaped probe is inside said tear duct;

taking hold of said wire proximal end section; and removing, by pulling from the eye side, said cannula out of the tear duct, said cannula sliding along the wire until reaching said wire intermediate section which then passes through said slot to release said cannula from said wire.

2. The method as defined in claim 1, wherein said space is made solid.

3. The method as defined in claim 2, wherein, at said lateral opening, said inner wall makes an angle with said longitudinal axis which is comprised between 15° and 30°.

4. The method as defined in claim 2, wherein said inner wall is planar.

5. The method as defined in claim 1, wherein, at said lateral opening, said inner wall makes an angle with said longitudinal axis which is comprised between 15° and 30°.

6. The method as defined in claim 1, wherein said inner wall is planar.

7. The method as defined in claim 1, wherein the size of a section of said wire is less than 0.5 mm.

8. The method as defined in claim 1, wherein said lateral opening is of elliptical shape.

9. A method for inserting a tube-shaped probe into a tear duct, comprising the steps of:

providing the tube-shaped probe being formed by a tube having a lateral wall defining the tube, wherein a terminating end of the tube has a thickness that varies to create a beveled form;

providing a wire, said wire having a distal end section, an intermediate narrowed section and a proximal end section;

connecting said wire distal end to said tube-shaped probe by inserting said wire distal end into said tube-shaped probe and connecting said wire distal end to said tube-shaped probe by a tight fit, adhesion, or ultrasonic welding;

providing a cannula, said cannula comprising an elongated hollow cylindrical body and extending along a longitudinal axis between a front end and a rear end, said elongated hollow cylindrical body having a front end opening at said front end, said front end opening having a dimension allowing passage therethrough of said wire, a slot extending from said front end towards said rear end, said slot having a slot width, as measured perpendicularly to said longitudinal axis, and being terminated by a lateral opening having a lateral width larger than said slot width, so that said proximal end section can pass through said lateral opening but not through said slot, said lateral opening being distant from said rear end, wherein said cannula comprises an inner wall defining a space inside the cannula between said lateral opening and said rear end, wherein said inner wall forms at said lateral opening an angle of less than 90° with said longitudinal axis, and wherein the cannula comprises a fin projecting laterally therefrom;

wherein said method comprises the further following steps of:

inserting said cannula into the tear duct by penetrating through an exterior entry point from the side of the eye up to an exit opening into the nasal cavity;

sliding said wire proximal end section inside said cannula from said front end opening towards said lateral opening until having said wire proximal end section coming out of said cannula through said lateral opening;

pulling from the eye side said cannula by the fin out of the tear duct while taking hold of said wire proximal end section which came out of said lateral opening;

inserting said wire distal end into said cannula, while taking hold of the cannula by the fin;

inserting said cannula and said wire distal end section into the tear duct from the exterior from the side of the eye until the wire proximal end section passing through the lateral opening comes out through the inside of the nostrils;

pulling said wire proximal end section out from said nostril, thereby advancing the said wire distal end and said tube-shaped probe connected thereto, until said tube-shaped probe is inside said tear duct;

taking hold of said wire proximal end section; and removing, by pulling on the fin from the eye side, said cannula out of the tear duct, said cannula sliding along the wire until reaching said wire intermediate section which then passes through said slot to release said cannula from said wire.

10. A method as defined in claim 9, wherein said fin is provided adjacent to said front end opening.

11. A method as defined in claim 9, wherein two fins are provided.

12. A method for inserting a tube-shaped probe into a tear duct, comprising the steps of:
- providing the tube-shaped probe being formed by a tube having a lateral wall defining a the tube, wherein a terminating end of the tube has a thickness that varies to create a beveled form;
- providing a wire, said wire having a distal end section, an intermediate narrowed section and a proximal end section;
- connecting said wire distal end to said tube-shaped probe by inserting said wire distal end into said tube-shaped probe and connecting said wire distal end to said tube-shaped probe by a tight fit, adhesion, or ultrasonic welding;
- providing a cannula, said cannula comprising an elongated hollow cylindrical body and extending along a longitudinal axis between a front end and a rear end, said elongated hollow cylindrical body having a front end opening at said front end, said front end opening having a dimension allowing passage therethrough of said wire, a slot extending from said front end towards said rear end, said slot having a slot width, as measured perpendicularly to said longitudinal axis, and being terminated by a lateral opening having a lateral width larger than said slot width, so that said proximal end section can pass through said lateral opening but not through said slot, said lateral opening being distant from said rear end, wherein said cannula comprises an inner wall defining a space inside the cannula between said lateral opening and said rear end, wherein said inner wall forms at said lateral opening an angle of less than 90° with said longitudinal axis, wherein said method comprises the further following steps of:
- inserting said cannula into the tear duct by penetrating through an exterior entry point from the side of the eye up to an exit opening into the nasal cavity;
- sliding said wire proximal end section inside said cannula from said front end opening towards said lateral opening until having said wire proximal end section coming out of said cannula through said lateral opening;
- pulling from the eye side said cannula out of the tear duct while taking hold of said wire proximal end section which came out of said lateral opening;
- inserting said wire distal end into said cannula, while taking hold of the cannula,
- inserting said cannula and said wire distal end section into the tear duct from the exterior from the side of the eye until the wire proximal end section passing through the lateral opening comes out through the inside of the nostrils,
- pulling said wire proximal end section out from said nostril, thereby advancing the said wire distal end and said tube-shaped probe connected thereto, until said probe is inside said tear duct;
- taking hold of said wire proximal end section;
- removing, by pulling from the eye side, said cannula out of the tear duct, said cannula sliding along the wire until reaching said wire intermediate section which then passes through said slot to release the cannula from the wire; and
- cutting any portion of the wire which hangs from the exterior of the nostril.

* * * * *